(12) United States Patent
Hilaire et al.

(10) Patent No.: US 7,641,684 B2
(45) Date of Patent: Jan. 5, 2010

(54) CATHETER SYSTEM FOR STENTING BIFURCATED VESSELS

(75) Inventors: Pierre Hilaire, Marly le Roi (FR); James J. Leary, Granite Bay, CA (US); Machiel Van Der Leest, Paris (FR)

(73) Assignee: Minvasys, SA, Gennevilliers (FR)

( * ) Notice: Subject to any disclaimer, the term of this patent is extended or adjusted under 35 U.S.C. 154(b) by 833 days.

(21) Appl. No.: 10/833,494

(22) Filed: Apr. 27, 2004

(65) Prior Publication Data

US 2005/0085845 A1 Apr. 21, 2005

Related U.S. Application Data

(60) Provisional application No. 60/512,259, filed on Oct. 16, 2003, provisional application No. 60/534,469, filed on Jan. 5, 2004.

(51) Int. Cl.
*A61F 2/06* (2006.01)

(52) U.S. Cl. .................................................. 623/1.35

(58) Field of Classification Search ................ 623/1.11, 623/1.12, 1.35, 1.36; 606/191–198; 604/96.01, 604/101.01, 101.02, 101.04
See application file for complete search history.

(56) References Cited

U.S. PATENT DOCUMENTS

| 4,896,670 | A | 1/1990 | Crittenden |
|---|---|---|---|
| 5,320,605 | A | 6/1994 | Sahota |
| 5,395,352 | A | 3/1995 | Penny |
| 5,613,980 | A | 3/1997 | Chauhan |
| 5,669,924 | A | 9/1997 | Shaknovich |
| 5,720,735 | A | 2/1998 | Dorros |
| 5,749,825 | A | 5/1998 | Fischell et al. |
| 5,755,771 | A | 5/1998 | Penn et al. |
| 5,891,154 | A * | 4/1999 | Loeffler ....................... 623/1.11 |
| 5,893,887 | A | 4/1999 | Jayaraman |
| 5,906,640 | A | 5/1999 | Penn et al. |
| 6,013,054 | A | 1/2000 | Yan |
| 6,086,611 | A | 7/2000 | Duffy et al. |
| 6,099,497 | A | 8/2000 | Adams et al. |
| 6,117,117 | A | 9/2000 | Mauch |
| 6,129,738 | A | 10/2000 | Lashinski et al. |
| 6,142,973 | A | 11/2000 | Carleton et al. |

(Continued)

FOREIGN PATENT DOCUMENTS

FR 2733689 7/1995

(Continued)

*Primary Examiner*—Kevin T Truong
(74) *Attorney, Agent, or Firm*—James J. Leary; GSS Law Group

(57) ABSTRACT

A catheter system and method are described for stenting a vessel at a bifurcation or sidebranch of the vessel. The catheter system includes a first balloon catheter, a second balloon catheter and a releasable linking device for holding the first and second balloon catheters arranged in a side-by-side configuration and aligned with one another along a longitudinal axis. The linking device allows the catheter system to be advanced as a unit and helps prevent premature or inadvertent dislodgement of the stent from the catheters, yet is releasable so that one or both of the balloon catheters can be released from the linking device and maneuvered separately from the rest of the catheter system when desired. The method utilizes the described catheter system for stenting bifurcated vessels using a modified "kissing balloons" technique.

53 Claims, 10 Drawing Sheets

U.S. PATENT DOCUMENTS

| | | | |
|---|---|---|---|
| 6,165,195 A | 12/2000 | Wilson et al. | |
| 6,210,380 B1 | 4/2001 | Mauch | |
| 6,221,098 B1 | 4/2001 | Wilson et al. | |
| 6,254,593 B1 | 7/2001 | Wilson | |
| 6,258,073 B1 | 7/2001 | Mauch | |
| 6,264,682 B1 | 7/2001 | Wilson et al. | |
| 6,325,826 B1 | 12/2001 | Vardi et al. | |
| 6,361,544 B1 | 3/2002 | Wilson et al. | |
| 6,371,978 B1 * | 4/2002 | Wilson | 623/1.35 |
| 6,383,213 B2 | 5/2002 | Wilson et al. | |
| 6,387,120 B2 | 5/2002 | Wilson et al. | |
| 6,428,567 B2 | 8/2002 | Wilson et al. | |
| 6,475,208 B2 | 11/2002 | Mauch | |
| 6,494,875 B1 | 12/2002 | Mauch | |
| 6,494,905 B1 | 12/2002 | Zedler et al. | |
| 6,508,836 B2 | 1/2003 | Wilson et al. | |
| 6,520,183 B2 * | 2/2003 | Amar | 604/96.01 |
| 6,520,988 B1 | 2/2003 | Colombo et al. | |
| 6,540,779 B2 | 4/2003 | Richter et al. | |
| 6,544,219 B2 | 4/2003 | Happ et al. | |
| 6,579,312 B2 | 6/2003 | Wilson et al. | |
| 2002/0055732 A1 | 5/2002 | Wilson | |
| 2002/0116047 A1 | 8/2002 | Vardi et al. | |
| 2002/0156516 A1 | 10/2002 | Vardi et al. | |
| 2002/0183763 A1 | 12/2002 | Callol et al. | |
| 2003/0028233 A1 | 2/2003 | Vardi et al. | |
| 2003/0097169 A1 | 5/2003 | Brucker et al. | |
| 2006/0100694 A1 * | 5/2006 | Globerman | 623/1.35 |

FOREIGN PATENT DOCUMENTS

| | | |
|---|---|---|
| WO | WO 9924104 A1 | 5/1999 |
| WO | WO 9944539 A2 | 9/1999 |
| WO | WO 0027307 A1 | 5/2000 |
| WO | WO 03053507 A1 | 7/2003 |

* cited by examiner

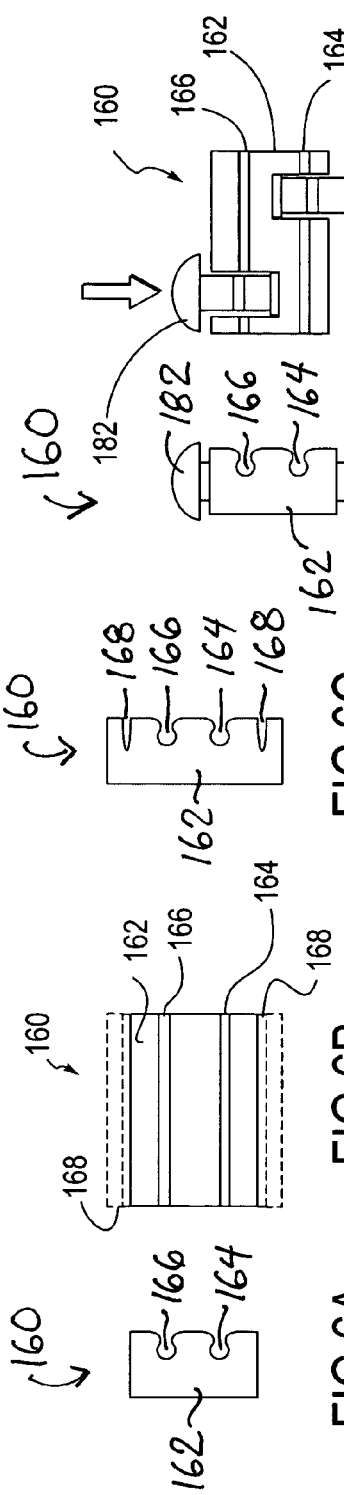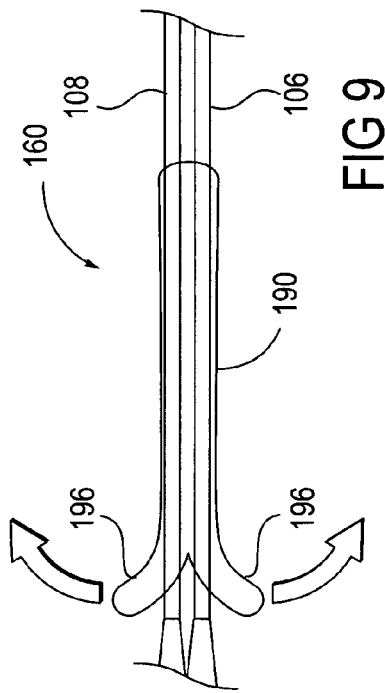

US 7,641,684 B2

CATHETER SYSTEM FOR STENTING BIFURCATED VESSELS

CROSS REFERENCE TO RELATED APPLICATIONS

This application claims the benefit of U.S. Provisional Application Ser. No. 60/512,259, filed Oct. 16, 2003, and U.S. Provisional Application Ser. No. 60/534,469, filed Jan. 5, 2004, the disclosures of which are incorporated by reference in their entirety.

FIELD OF THE INVENTION

The present invention relates generally to catheters and catheter systems for performing angioplasty and vascular stenting. More particularly it relates to a catheter system and method for stenting a vessel at a bifurcation or sidebranch of the vessel.

BACKGROUND OF THE INVENTION

The following patents and patent applications relate to catheters and catheter systems for performing angioplasty and stenting of bifurcated vessels. These and all patents and patent applications referred to herein are incorporated by reference in their entirety.
U.S. Pat. No. 6,579,312 Stent and catheter assembly and method for treating bifurcations
U.S. Pat. No. 6,540,779 Bifurcated stent with improved side branch aperture and method of making same
U.S. Pat. No. 6,520,988 Endolumenal prosthesis and method of use in bifurcation regions of body lumens
U.S. Pat. No. 6,508,836 Stent and catheter assembly and method for treating bifurcations
U.S. Pat. No. 6,494,875 Bifurcated catheter assembly
U.S. Pat. No. 6,475,208 Bifurcated catheter assembly
U.S. Pat. No. 6,428,567 Stent and catheter assembly and method for treating bifurcations
U.S. Pat. No. 6,387,120 Stent and catheter assembly and method for treating bifurcations
U.S. Pat. No. 6,383,213 Stent and catheter assembly and method for treating bifurcations
U.S. Pat. No. 6,371,978 Bifurcated stent delivery system having retractable sheath
U.S. Pat. No. 6,361,544 Stent and catheter assembly and method for treating bifurcations
U.S. Pat. No. 6,325,826 Extendible stent apparatus
U.S. Pat. No. 6,264,682 Bifurcated stent delivery system having retractable sheath
U.S. Pat. No. 6,258,073 Bifurcated catheter assembly
U.S. Pat. No. 6,254,593 Bifurcated stent delivery system having retractable sheath
U.S. Pat. No. 6,221,098 Stent and catheter assembly and method for treating bifurcations
U.S. Pat. No. 6,210,380 Bifurcated catheter assembly
U.S. Pat. No. 6,165,195 Stent and catheter assembly and method for treating bifurcations
U.S. Pat. No. 6,142,973 Y-shaped catheter
U.S. Pat. No. 6,117,117 Bifurcated catheter assembly
U.S. Pat. No. 6,086,611 Bifurcated stent
U.S. Pat. No. 5,720,735 Bifurcated endovascular catheter
U.S. Pat. No. 5,669,924 Y-shuttle stent assembly for bifurcating vessels and method of using the same
U.S. Pat. No. 5,613,980 Bifurcated catheter system and method
U.S. Pat. No. 6,013,054 Multifurcated balloon catheter
U.S. Pat. No. 4,896,670 Kissing balloon catheter
U.S. Pat. No. 5,395,352 Y-adaptor manifold with pinch valve for an intravascular catheter
U.S. Pat. No. 6,129,738 Method and apparatus for treating stenoses at bifurcated regions
U.S. Pat. No. 6,544,219 Catheter for placement of therapeutic devices at the ostium of a bifurcation of a body lumen
U.S. Pat. No. 6,494,905 Balloon catheter
U.S. Pat. No. 5,749,825 Means method for treatment of stenosed arterial bifurcations
U.S. Pat. No. 5,320,605 Multi-wire multi-balloon catheter
U.S. Pat. No. 6,099,497 Dilatation and stent delivery system for bifurcation lesions
U.S. Pat. No. 5,720,735 Bifurcated endovascular catheter
U.S. Pat. No. 5,906,640 Bifurcated stent and method for the manufacture and delivery of same
U.S. Pat. No. 5,893,887 Stent for positioning at junction of bifurcated blood vessel and method of making
U.S. Pat. No. 5,755,771 Expandable stent and method of delivery of same
US 20030097169A1 Bifurcated stent and delivery system
US 20030028233A1 Catheter with attached flexible side sheath
US 20020183763A1 Stent and catheter assembly and method for treating bifurcations
US 20020156516A1 Method for employing an extendible stent apparatus
US 20020116047A1 Extendible stent apparatus and method for deploying the same
US 20020055732A1 Catheter assembly and method for positioning the same at a bifurcated vessel
WO 9944539A2 Dilatation and stent delivery system for bifurcation lesions
WO 03053507 Branched balloon catheter assembly
WO 9924104 Balloon catheter for repairing bifurcated vessels
WO 0027307 The sheet expandable trousers stent and device for its implantation
FR 2733689 Endoprosthesis with installation device for treatment of blood-vessel bifurcation stenosis

SUMMARY OF THE INVENTION

The present invention relates generally to catheters and catheter systems for performing angioplasty and vascular stenting. More particularly it relates to a catheter system and method for stenting a vessel at a bifurcation or sidebranch of the vessel.

In a first aspect, the invention comprises a catheter system for stenting bifurcated vessels. The catheter system includes a first balloon catheter, a second balloon catheter and a linking device for holding the first and second balloon catheters in a side-by-side configuration and aligned with one another along a longitudinal axis. The catheter system may include one or more vascular stents of various configurations mounted on the first and/or second balloon catheters. The linking device allows the catheter system to be advanced as a unit and helps prevent premature or inadvertent dislodgement of the stent from the catheters. Typically, the catheter system will also include a first and second steerable guidewire for guiding the first and second balloon catheters within the patient's blood vessels. Optionally, the linking device may also be configured to hold one or both of the guidewires stationary with respect to the catheter system.

The catheter system may be arranged with the inflatable balloons in a side-by-side configuration for stenting the bifurcated vessels using a method similar to the "kissing balloons"

technique. Alternatively, the catheter system may be arranged with the inflatable balloons in a low-profile staggered or tandem configuration for stenting the bifurcated vessels using a modified "kissing balloons" technique. When arranged in the staggered or tandem configuration, the second balloon catheter may optionally be constructed with a flexible tubular extension that extends the guidewire lumen distally from the inflatable balloon.

In a second aspect, the invention comprises a linking device for holding the first and second balloon catheters of the system in a side-by-side configuration and aligned with one another along a longitudinal axis. The linking device allows the catheter system to be advanced as a unit and helps prevent premature or inadvertent dislodgement of the stent from the catheters. Optionally, the linking device may also be configured to hold one or both of the guidewires stationary with respect to the catheter system. The linking device is preferably releasable so that one or both of the balloon catheters and/or the guidewires can be released from the linking device and maneuvered separately from the rest of the catheter system. In one embodiment the linking device is self-releasing in the sense that the linking device demounts itself from the first and second balloon catheters as the catheter system is advanced into the patient's body.

In a third aspect, the invention comprises a method for stenting bifurcated vessels utilizing the described catheter system. In a first variation of the method, the inflatable balloons are arranged in a side-by-side configuration for stenting the bifurcated vessels in a method similar to the "kissing balloons" technique, but utilizing a linking device for holding the first and second balloon catheters in a side-by-side configuration and aligned with one another along a longitudinal axis. In a second variation of the method, the inflatable balloons are arranged in a staggered or tandem configuration for stenting the bifurcated vessels using a modified "kissing balloons" technique that also utilizes a linking device for holding the first and second balloon catheters in a side-by-side configuration and aligned with one another along a longitudinal axis. When desired, the linking device may be released so that one or both of the balloon catheters and/or the guidewires can be maneuvered separately from the rest of the catheter system.

BRIEF DESCRIPTION OF THE DRAWINGS

FIGS. 6A-9 show various embodiments of a linking device for use with the catheter system of the present invention.

DETAILED DESCRIPTION OF THE INVENTION

Figure 1:
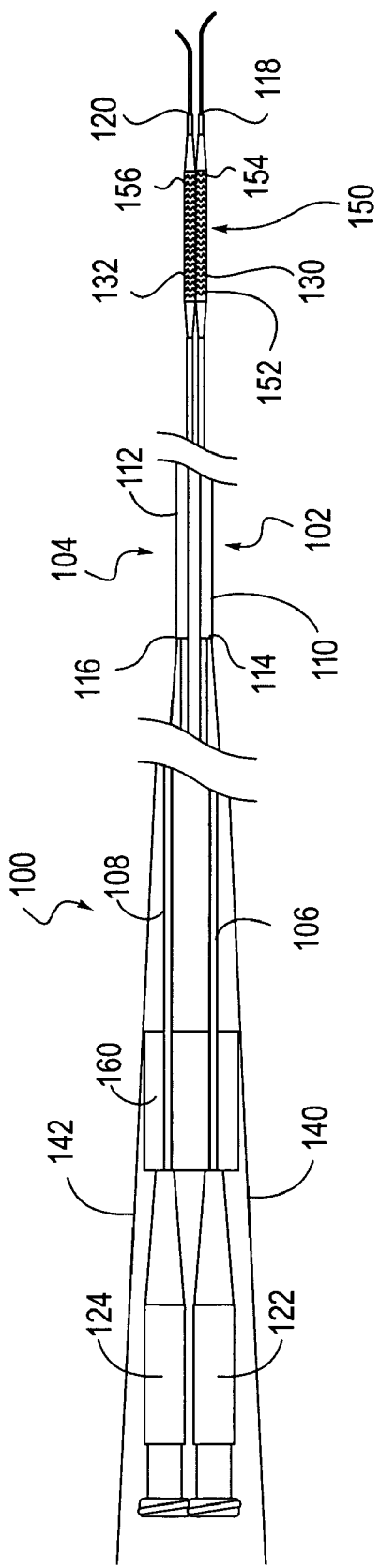
FIG. 1 shows a first embodiment of a catheter system for stenting bifurcated vessels according to the present invention.

FIG. 1 shows a first embodiment of the catheter system 100 of the present invention for stenting bifurcated vessels. The catheter system 100 includes a first balloon catheter 102 and a second balloon catheter 104. An inflatable balloon 130, 132 is mounted on each of the first and second balloon catheters 102, 104 near the distal end of the catheters. A balloon-expandable vascular stent 150 is mounted on the catheter system 100, typically by crimping or swaging the stent 150 over both of the inflatable balloons 130, 132. The stent structure is shown generically and is not intended to be limited to any particular strut geometry. Typically, the catheter system 100 will also include a first and second steerable guidewire 140, 142 for guiding the first and second balloon catheters 102, 104 within the patient's blood vessels. The first and second steerable guidewires 140, 142 will typically have a diameter of 0.010-0.018 inches (approximately 0.25-0.46 mm), preferably 0.014 inches (approximately 0.36 mm). A linking device 160 releasably joins the first balloon catheter 102 and the second balloon catheter 104 together near the proximal ends of the catheters. The linking device 160 holds the first and second balloon catheters 102, 104 in a side-by-side configuration and aligned with one another along a longitudinal axis. The linking device 160 allows the catheter system 100 to be advanced as a unit and helps prevent premature or inadvertent dislodgement of the stent 150 from the catheters. Optionally, the linking device 160 may also be configured to hold one or both of the guidewires 140, 142 stationary with respect to the catheter system 100.

The first and second balloon catheters 102, 104 may be of any known construction for balloon angioplasty or stent delivery catheters, including rapid exchange and over-the-wire catheter constructions. In a particularly preferred embodiment, the first and second balloon catheters are constructed as rapid exchange catheters, wherein a proximal section 106, 108 of each catheter is constructed of hypodermic tubing, which may be formed from stainless steel, a superelastic nickel-titanium or titanium-molybdenum alloy or the like. The exterior of the proximal section 106, 108 is preferably coated with PTFE or another highly lubricious coating. A proximal connector 122, 124, such as a luer lock connector or the like, is attached at the proximal end of the proximal section 106, 108 and communicates with a balloon inflation lumen that extends through the hypodermic tubing. Each catheter includes a flexible distal section 110, 112 joined to the proximal section 106, 108. Typically, the flexible distal section 110, 112 has two lumens that extend through most of its length, including a guidewire lumen that extends from a proximal guidewire port 114, 116 to a distal port 118, 120 at the distal end of the catheter, and a balloon inflation lumen that connects from the balloon inflation lumen of the proximal section 106, 108 to the interior of the inflatable balloon 130, 132, which is mounted near the distal end of the flexible distal section 110, 112. The first and second inflatable balloons 130, 132 may have the same length and diameter and pressure compliance or they may have different lengths, diameters and/or pressure compliances, depending on the geometry of the target vessel that the catheter system 100 is intended for. The inflatable balloons 130, 132 may be made from a variety of known angioplasty balloon materials, including, but not limited to, PVC, polyethylene, polyolefin, polyamide, polyester, PET, PBT, and blends, alloys, copolymers and composites thereof. The first and second inflatable balloons 130, 132 may be made from the same material or different materials. The flexible distal section 110, 112 is typically constructed of flexible polymer tubing and may have a coaxial or multilumen construction. Preferably, one, two or more radiopaque markers are mounted on the flexible distal section 110, 112 to indicate the location of the inflatable balloons 130, 132 under fluoroscopic imaging. A transition element may be included to create a gradual transition in stiffness between the proximal section 106, 108 and the flexible distal section 110, 112, and to avoid a stress concentration at the juncture between the two sections. The transition element may be constructed as a tapered or spiral wound element that is formed as an extension of the hypodermic tubing or from a separate piece of wire or tubing.

In this illustrative example, the catheter system 100 is configured for delivering a Y-shaped bifurcated stent 150. The bifurcated stent 150 has a main trunk 152 connected to first and second sidebranches 154, 156 of the stent. The catheter system 100 is prepared for use by inserting the inflatable balloons 130, 132 in a deflated and folded state through the main trunk 152 of the bifurcated stent 150, with one balloon extending into each of the first and second sidebranches 154, 156. The bifurcated stent 150 is then crimped or swaged over the inflatable balloons 130, 132. A support wire may be inserted into each of the guidewire lumens to support them during the crimping or swaging step. The proximal sections 106, 108 of the catheters are inserted into the linking device 160 to hold the first and second balloon catheters 102, 104 in a side-by-side configuration and aligned with one another along a longitudinal axis. This preparation may be carried out at the manufacturing facility or it may be performed at the point of use by a medical practitioner.

Figure 2:
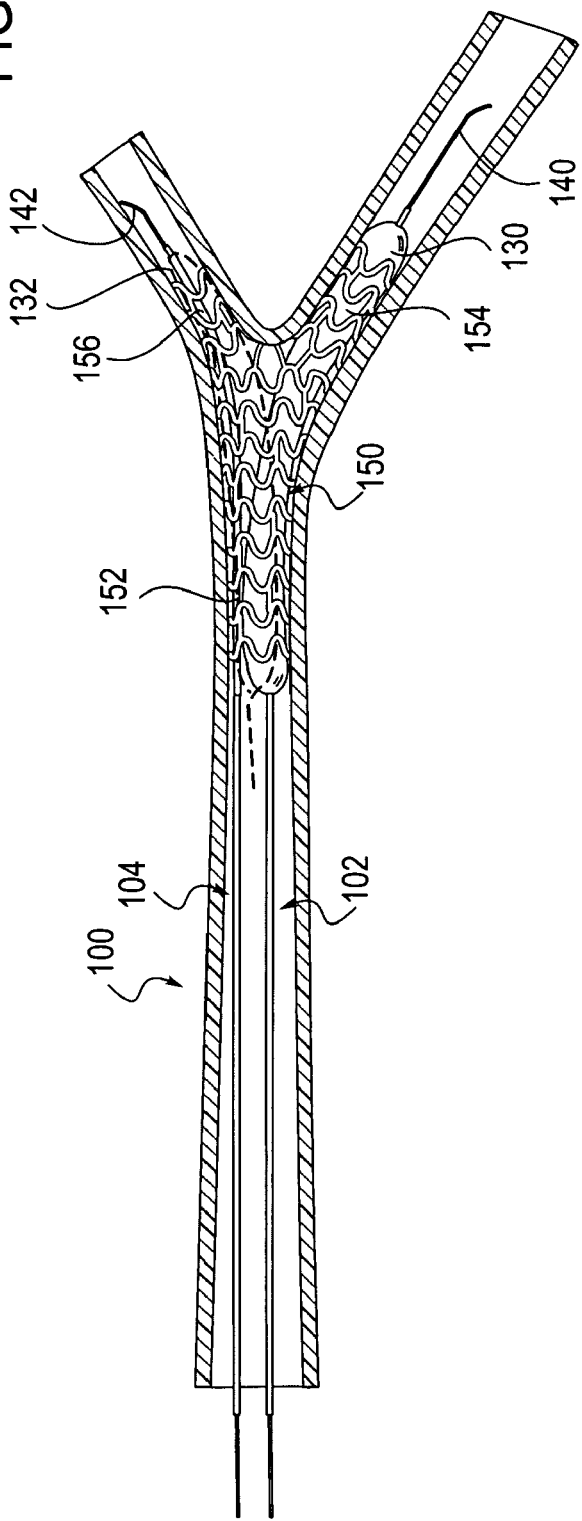
FIG. 2 shows the catheter system of FIG. 1 in use for stenting a bifurcated vessel with a bifurcated stent.

FIG. 2 shows the catheter system 100 of FIG. 1 in use for stenting a bifurcated vessel. The catheter system 100 is inserted into a body lumen that is desired to be stented and advanced to the point of the bifurcation. For stenting coronary arteries or carotid arteries, the catheter system 100 is typically inserted through a guiding catheter that has been previously positioned at the ostium of the target vessel. For stenting in peripheral arteries or other body lumens, the catheter system 100 may be inserted directly into the vessel, for example using the Seldinger technique or an arterial cutdown, or it may be inserted through an introducer sheath or guiding catheter placed into the vessel. The first and second balloon catheters 102, 104 are maneuvered with the help of the steerable guidewires 140, 142 so that the first and second inflatable balloons 130, 132, with the first and second sidebranches 154, 156 of the stent 150 mounted thereon, extend into the respective first and second sidebranches of the bifurcated vessel. The first and second inflatable balloons 130, 132 are inflated separately and/or together to expand the stent 150 and to seat it securely within the vessel, as shown in FIG. 2. This is similar to the "kissing balloons" technique that has been previously described in the literature. An advantage of the present invention over prior methods is that the linking device 160 allows the catheter system 100 to be advanced as a unit and helps prevent premature or inadvertent dislodgement of the stent 150 from the catheters.

Once the stent 150 has been deployed, both balloons 130, 132 are deflated and the catheter system 100 is withdrawn from the patient. Alternatively, one or both of the balloon catheters 102, 104 can be released from the linking device 160 and used separately for dilating and/or stenting other vessels upstream or downstream of the stent 150.

Figure 3:
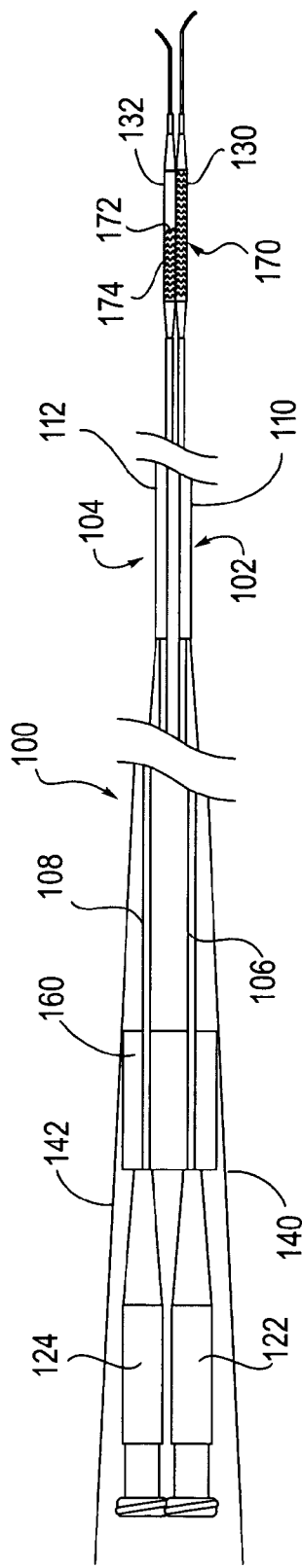
FIG. 3 shows a variation of the catheter system of FIG. 1 for stenting a bifurcated vessel.

FIG. 3 shows a variation of the catheter system 100 of the present invention for stenting a bifurcated vessel. The construction of the catheter system 100 is very similar to the catheter system described above in connection with FIG. 1 with the exception that the system utilizes a straight, i.e. non-bifurcated, stent 170. The stent structure is shown generically and is not intended to be limited to any particular strut geometry. In one particularly preferred embodiment, the stent 170 is in the form of an open-cell stent, having a cylindrical body 174 with one or more side openings 172 that are suitable for placement at a bifurcation or sidebranch of the vessel without hindering blood flow into the sidebranch. Because of their flexibility and open structure, open-cell stents are well suited for stenting bifurcated vessels. The side openings 172 can be expanded or remodeled with a dilatation balloon inserted through the side opening or with two dilatation balloons, using the "kissing balloons" technique. A closed-cell stent with large side openings and/or expandable side openings may also be utilized. Alternatively, the catheter system may utilize a side-hole stent intended for stenting bifurcations or for stenting a main vessel at the location of a sidebranch vessel. In this case, the stent has an approximately cylindrical body with a side hole intended to be positioned at the site of a sidebranch vessel. The side hole may be preformed in the stent or it may be a slit or a potential hole that can be expanded to form a side hole.

The catheter system 100 is prepared for use by inserting the inflatable balloons 130, 132 in a deflated and folded state into the stent 170, with the first balloon 130 extending all the way through the cylindrical body 174 and the second balloon 132 exiting the cylindrical body 174 at the side opening 172 that is intended to be positioned at the bifurcation or sidebranch vessel. Alternatively, the second balloon 132 may be positioned proximal to the side opening 172 so that only the distal tip of the catheter 104 or only the guidewire 142 exits the cylindrical body 174 at the side opening 172 to decrease the distal crossing profile of the catheter system 100. The stent 170 is then crimped or swaged over the inflatable balloons 130, 132. A support wire may be inserted into each of the guidewire lumens to support them during the crimping or swaging step. The proximal sections 106, 108 of the catheters are inserted into the linking device 160 to hold the first and second balloon catheters 102, 104 in a side-by-side configuration and aligned with one another along a longitudinal axis. This preparation may be carried out at the manufacturing facility or it may be performed at the point of use by a medical practitioner.

Figure 4:
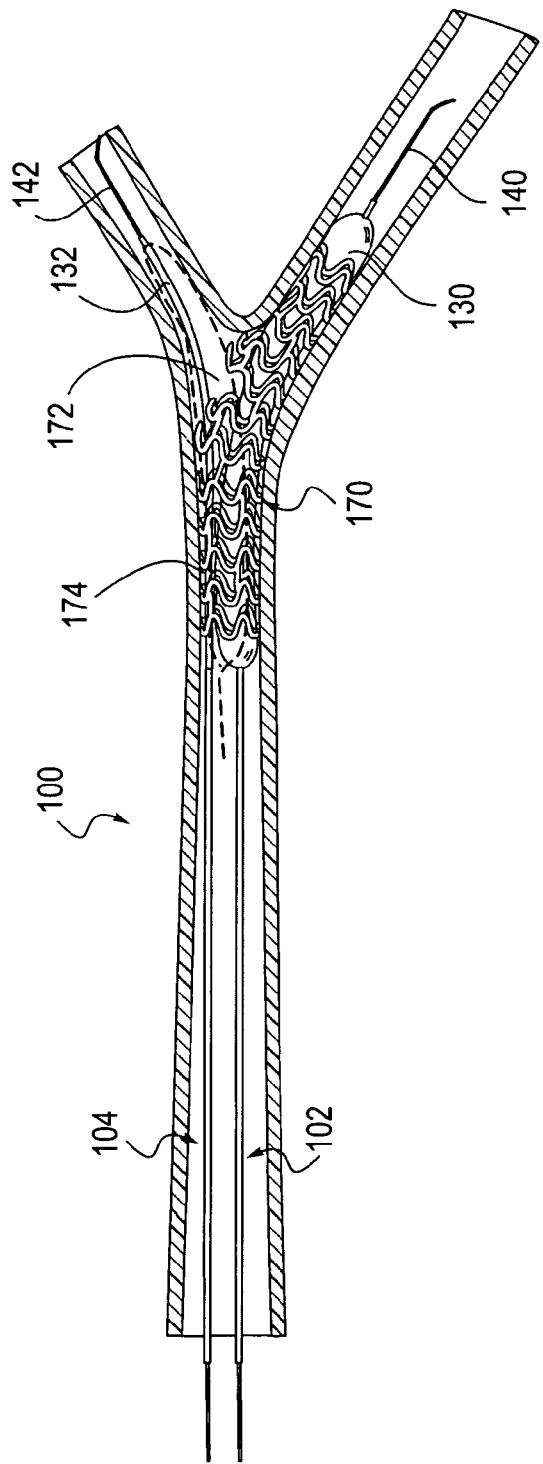
FIG. 4 shows the catheter system of FIG. 3 in use for stenting a bifurcated vessel.

FIG. 4 shows the catheter system 100 of FIG. 3 in use for stenting a bifurcated vessel. The catheter system 100 is inserted into a body lumen that is desired to be stented and advanced to the point of the bifurcation. For stenting coronary arteries or carotid arteries, the catheter system 100 is typically inserted through a guiding catheter that has been previously positioned at the ostium of the target vessel. For stenting in peripheral arteries or other body lumens, the catheter system 100 may be inserted directly into the vessel, for example using the Seldinger technique or an arterial cutdown, or it may be inserted through an introducer sheath or guiding catheter placed into the vessel. The first and second balloon catheters 102, 104 are maneuvered with the help of the steerable guidewires 140, 142 so that the first and second inflatable balloons 130, 132, with the stent mounted thereon, extend into the respective first and second sidebranches of the bifurcated vessel. The first inflatable balloon 130 will typically be positioned in the larger of the two sidebranches or in the main lumen of the vessel at the location of a smaller sidebranch vessel. The first inflatable balloon 130 is inflated to expand the stent and to seat it securely within the vessel, as shown in FIG. 4. Then, the first inflatable balloon 130 is deflated and the second inflatable balloon 132 is inflated to expand the side opening 172 at the location of the second sidebranch vessel. Optionally, the first and second inflatable balloons 130, 132 may be inflated simultaneously using the "kissing balloons" technique.

Once the stent 170 has been deployed, both balloons 130, 132 are deflated and the catheter system 100 is withdrawn from the patient. Alternatively, one or both of the balloon catheters 102, 104 can be released from the linking device 160 and used separately for dilating and/or stenting other vessels upstream or downstream of the stent 170. Optionally, a sidebranch stent may be placed in the second sidebranch vessel before or after deployment of the stent 170.

Figure 5:
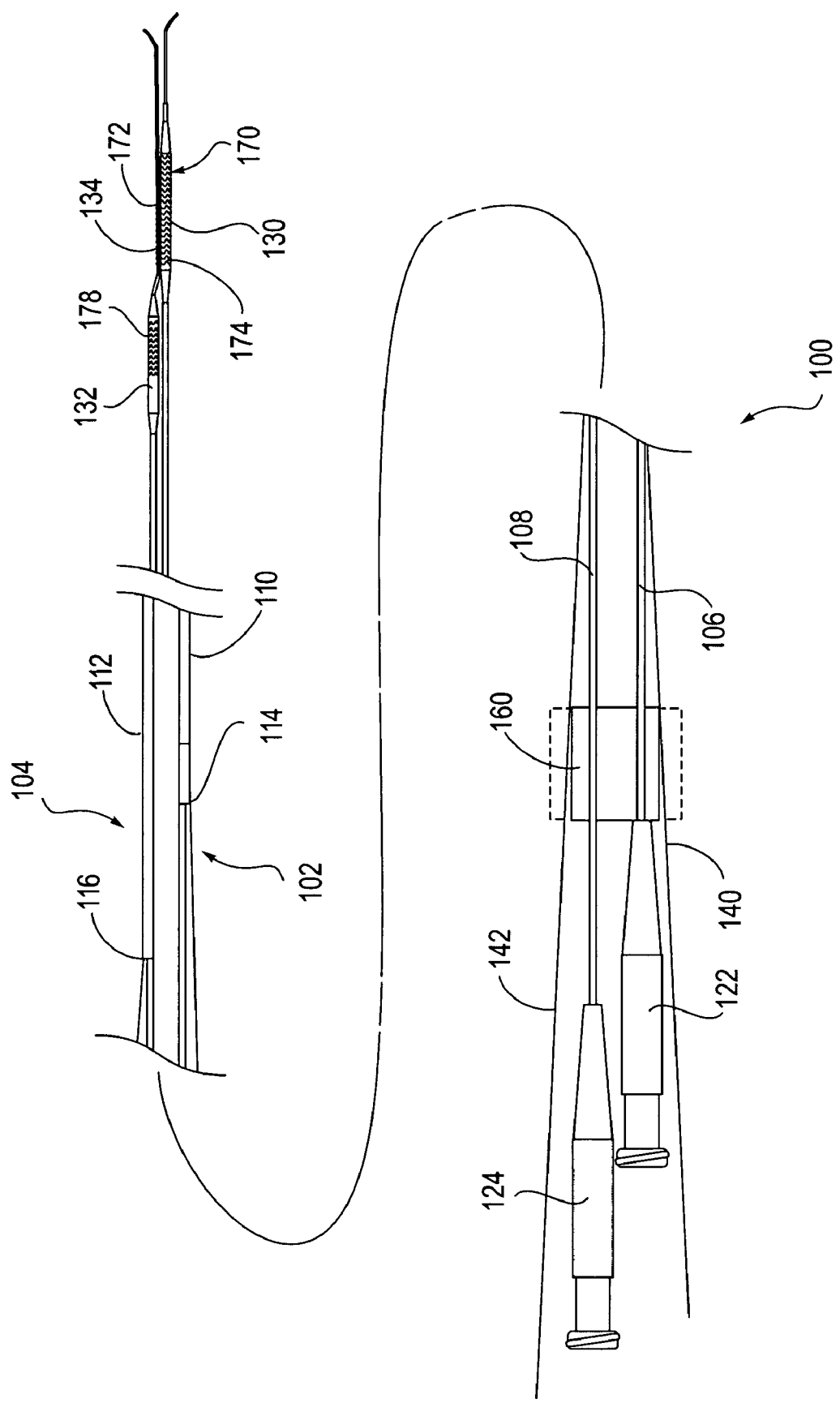
FIG. 5 shows a second embodiment of a catheter system for stenting bifurcated vessels.

FIG. 5 shows a second embodiment of the catheter system 100 for stenting bifurcated vessels. The construction of the catheter system 100 is very similar to the catheter system described above in connection with FIGS. 1 and 3, with the exception that the second balloon catheter 104 is constructed with a flexible tubular extension 134 connected to the distal end of the catheter. The guidewire lumen extends through the flexible tubular extension 134. The flexible tubular extension 134 allows the first and second inflatable balloons 130, 132 to be assembled together in a staggered or tandem initial position. This variation of the catheter system 100 utilizes a main stent 170, which is typically a straight, i.e. non-bifurcated, stent, as described above. In addition, the catheter system 100 may optionally utilize a sidebranch stent 178. The stent structures are shown generically and are not intended to be limited to any particular strut geometry. These distal features of the catheter system 100 can be seen in greater detail in the enlarged view of FIG. 10.

The catheter system 100 is prepared for use by first inserting the second inflatable balloon 132 in a deflated and folded state through the optional sidebranch stent 178 and crimping or swaging the sidebranch stent 178 over the second inflatable balloon 132. Alternatively, the sidebranch stent 178 may be mounted on a separate balloon catheter for use with the catheter system 100. The first inflatable balloon 130 is then inserted in a deflated and folded state into the main stent 170, with the first balloon 130 extending all the way through the cylindrical body 174. The flexible tubular extension 134 of the second balloon catheter 104 is inserted into the main stent 170 alongside the first balloon 130 with the flexible tubular extension 134 exiting the cylindrical body 174 at the side opening 172 that is intended to be positioned at the bifurcation or sidebranch vessel. Preferably, the flexible tubular extension 134 terminates at the side opening 172 of the main stent 170 to reduce the crossing profile of the distal portion of the stent 170. Alternatively, the flexible tubular extension 134 may extend distally from the side opening 172 if desired. The main stent 170 is then crimped or swaged over the first inflatable balloon 130 and the flexible tubular extension 134. A support wire may be inserted into each of the guidewire lumens to support them during the crimping or swaging step. The proximal sections 106, 108 of the catheters are inserted into the linking device 160 to hold the first and second balloon catheters 102, 104 in a side-by-side configuration and in a desired alignment with one another along the longitudinal axis. This preparation may be carried out at the manufacturing facility or it may be performed at the point of use by a medical practitioner.

In an alternate embodiment of the catheter system 100 of FIG. 5, the second balloon catheter 104 may be constructed without a flexible tubular extension 134. In this case, the distal tip of the second balloon catheter 104 would be positioned proximal to the main stent 170 and the second steerable guidewire 142 would be inserted into the main stent 170 alongside the first balloon 130 with the guidewire 142 exiting the cylindrical body 174 at the side opening 172. This would provide an even lower crossing profile for the catheter system 100.

FIGS. 6A-9 show various embodiments of a linking device 160 for use with the catheter system 100 of the present invention. FIG. 6A shows an end view and 6B shows a front view of a first embodiment of a linking device 160. The linking device 160 has a body 162 with a first channel 164 and a second channel 166 extending along a surface of the body in a side-by-side configuration, preferably with the first and second channels 164, 166 approximately parallel to one another. The first and second channels 164, 166 are preferably undercut and sized to have a captive interference fit with the proximal sections 106, 108 of the first and second balloon catheters 102, 104. The linking device 160 is preferably molded of a flexible polymer or elastomer with a high coefficient of friction so that it effectively grips the proximal sections 106, 108 of the first and second balloon catheters 102, 104 when they are inserted into the first and second channels 164, 166. In use, the linking device 160 holds the first and second balloon catheters 102, 104 arranged in a side-by-side configuration and aligned with one another along a longitudinal axis. The linking device 160 allows the catheter system 100 to be advanced as a unit and helps prevent premature or inadvertent dislodgement of the stent from the catheters. When it is desired, one or both of the balloon catheters 102, 104 can be released from the linking device 160 and maneuvered separately from the rest of the catheter system 100.

Optionally, the linking device 160 of FIG. 6B may also be configured to hold one or both of the guidewires 140, 142 stationary with respect to the catheter system 100. In this case, the body 162 of the linking device 160 would include one or two slots 168, shown in dashed lines in FIG. 6B, that are sized and configured to create a captive interference fit with the proximal section of the guidewires 140, 142. FIG. 6C shows an end view of the linking device 160 with optional slots 168 for holding the guidewires 140, 142. When it is desired, the guidewires 140, 142 can be released from the linking device 160 and maneuvered separately from the rest of the catheter system 100.

In an alternative embodiment, the linking device 160 of FIGS. 6A-6B may be permanently attached to one of the balloon catheters and releasably attached to the other. In another alternative embodiment, the linking device 160 may be configured to attach instead to the proximal connectors 122, 124 of the balloon catheters 102, 104 or it may be molded into the proximal connectors 122, 124.

FIG. 7A shows an end view and 7B shows a front view of a second embodiment of the linking device 160. The linking device 160 has a body 162 with a first channel 164 and a second channel 166 extending along one surface of the body in a side-by-side configuration, preferably with the first and second channels 164, 166 approximately parallel to one another. The first and second channels 164, 166 are preferably undercut and sized to have a captive sliding fit with the proximal sections 106, 108 of the first and second balloon catheters 102, 104. A first locking device 180 is associated with the first channel 164, and a second locking device 182 is associated with the second channel 166. The first and second locking devices 180, 182 are configured to releasably lock the proximal sections 106, 108 of the first and second balloon catheters 102, 104 in a desired alignment with one another along the longitudinal axis. Each of the locking devices 180, 182 will typically include a spring or other biasing member to hold the locking device in a locked position and a push button or other actuating member to release the locking device. The linking device 160 allows the catheter system 100 to be advanced as a unit and helps prevent premature or inadvertent dislodgement of the stent from the catheters. When it is desired, one or both of the locking devices 180, 182 can be released to allow one of the balloon catheters 102, 104 to be advanced or retracted with respect to the other to adjust their longitudinal alignment. In addition, one or both of the balloon catheters 102, 104 can be released completely from the linking device 160 and maneuvered separately from the rest of the catheter system 100.

Optionally, the linking device 160 of FIGS. 7A-7B may also be configured to hold one or both of the guidewires 140, 142 stationary with respect to the catheter system 100. In this case, the body 162 of the linking device 160 would include one or two additional locking devices, or slots or other structures configured to grip the proximal section of the guidewires 140, 142. When it is desired, the guidewires 140, 142 can be released from the linking device 160 and maneuvered separately from the rest of the catheter system 100.

In an alternative embodiment, the linking device 160 of FIGS. 7A-7B may be permanently attached to one of the balloon catheters and releasably attached to the other.

FIG. 8A shows an end view and 8B shows a front view of a third embodiment of the linking device 160. The linking device 160 has a first linking member 184 attached to the proximal section 106 of the first balloon catheter 102 and a second linking member 186 attached to the proximal section 108 of the second balloon catheter 104. The first linking member 184 and the second linking member 186 have interlocking features so that the two catheters can be releasably attached to one another. In the example shown, the interlocking features are corresponding male 187 and female 185 elements that can be attached and detached to one another in the manner of a snap or zip-lock device. FIG. 8C shows an end view of the linking device 160 with the first linking member 184 and the second linking member 186 detached from one another. Optionally, the linking device 160 can be configured so that the balloon catheters 102, 104 can be attached to one another in different longitudinal alignments. In other embodiments, the linking device 160 of FIGS. 8A-8C may utilize alternative interlocking features such as clamps, snaps, hook-and-loop fasteners, a releasable adhesive, a repositionable adhesive, etc.

Optionally, the linking device 160 of FIGS. 8A-8C may also be configured to hold one or both of the guidewires 140, 142 stationary with respect to the catheter system 100. In this case, one or both of the linking members 184, 186 would include a locking device, slot or other structure configured to hold the proximal section of one of the guidewires 140, 142. This configuration would allow each guidewire and balloon catheter pair to be moved as a unit separately from the rest of the catheter system 100 when the linking members 184, 186 are separated. When it is desired, one or both of the guidewires 140, 142 can be released from the linking members 184, 186 and maneuvered separately from the rest of the catheter system 100.

FIG. 9 shows a fourth embodiment of the linking device 160 that utilizes a peel-away sheath 190 for attaching the proximal sections 106, 108 of the first and second balloon catheters 102, 104 together. The peel-away sheath 190 may be made from heat shrink polymer tubing that is heat shrunk onto the proximal sections 106, 108 of the first and second balloon catheters 102, 104 to lock them together in a desired alignment with one another along the longitudinal axis. The peel-away sheath 190 has tabs or handles 196 to facilitate peeling the peel-away sheath 190 apart to release the balloon catheters 102, 104 so that they can be maneuvered separately from one another. The peel-away sheath 190 may utilize features, such as polymer orientation, perforations and/or an incised groove, to assure that the peel-away sheath 190 will peel apart along a longitudinal dividing line.

FIGS. 10-13 show the catheter system 100 of FIG. 5 in use for stenting a bifurcated vessel using a main stent 170 and a sidebranch stent 178. The catheter system 100 is inserted into a body lumen that is desired to be stented and advanced to the point of the bifurcation. For stenting coronary arteries or carotid arteries, the catheter system 100 is typically inserted through a guiding catheter that has been previously positioned at the ostium of the target vessel. For stenting in peripheral arteries or other body lumens, the catheter system 100 may be inserted directly into the vessel, for example using the Seldinger technique or an arterial cutdown, or it may be inserted through an introducer sheath or guiding catheter placed into the vessel. The staggered or tandem initial position of the first and second inflatable balloons 130, 132 provides a very low crossing profile. The low crossing profile allows the catheter system 100 with a 3.0 or 3.5 mm (expanded diameter) coronary stent 170 mounted on it to be delivered through a 6 French (approximately 2 mm external diameter) guiding catheter, which will typically have an internal diameter of 0.066-0.071 inches (approximately 1.68-1.80 mm internal diameter).

Figure 10:
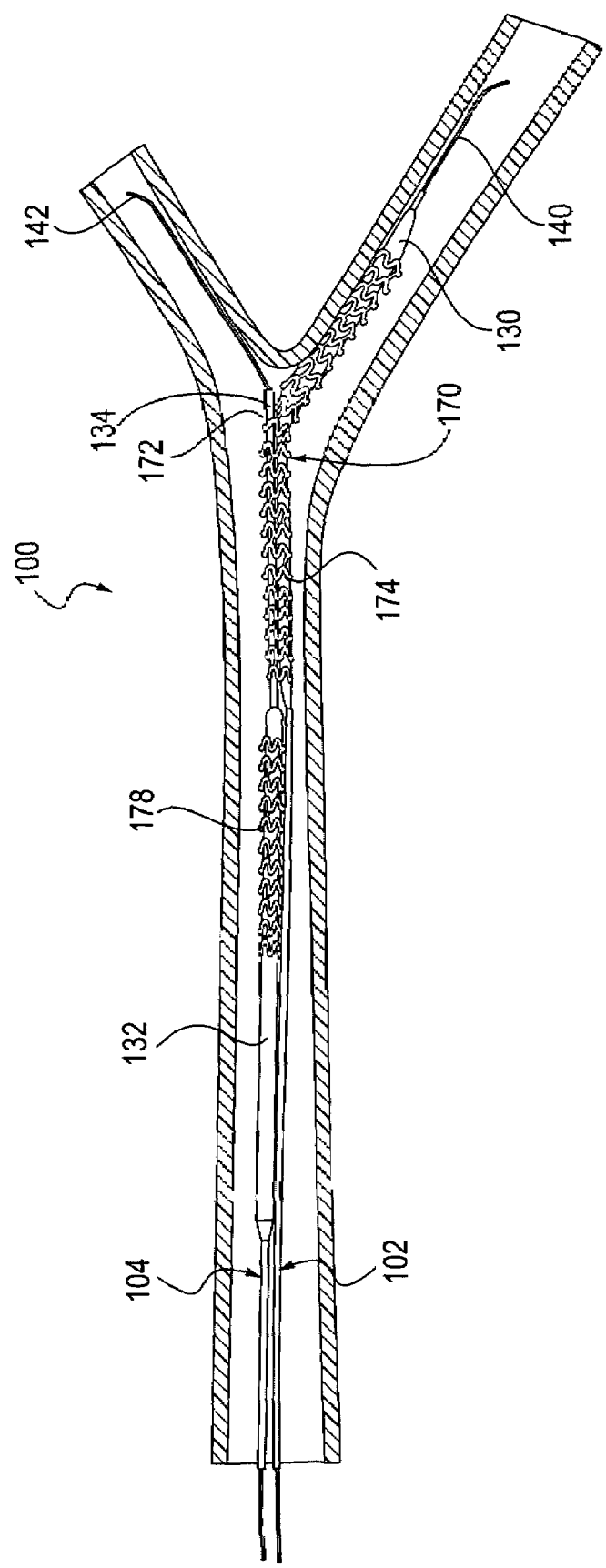
FIGS. 10-13 show the catheter system of FIG. 5 in use for stenting a bifurcated vessel using a main stent and a side-branch stent.

The catheter system 100 is maneuvered with the help of the steerable guidewires 140, 142 so that the first inflatable balloon 130, with the main stent 170 mounted on it, extends into the first sidebranch of the bifurcated vessel and the second steerable guidewire 142 extends into the second sidebranch, as shown in FIG. 10. The first inflatable balloon 130 will typically be positioned in the larger of the two sidebranches or in the main lumen of the vessel at the location of a smaller sidebranch vessel.

When advancing the catheter system 100, the second steerable guidewire 142 may be positioned with its distal tip withdrawn into the flexible tubular extension 134 of the second balloon catheter 104 until the catheter system 100 reaches the bifurcation so that it will not be inadvertently damaged or interfere with advancement of the catheter system 100. This can be facilitated by inserting the proximal section of the second guidewire 142 into the optional slot or locking device 168 on the linking device 160. When the distal tip of the second balloon catheter 104 is in the vicinity of the sidebranch vessel, the second steerable guidewire 142 can be released from the linking device 160 and advanced with its distal tip extending from the flexible tubular extension 134 to engage the sidebranch vessel.

Figure 11:
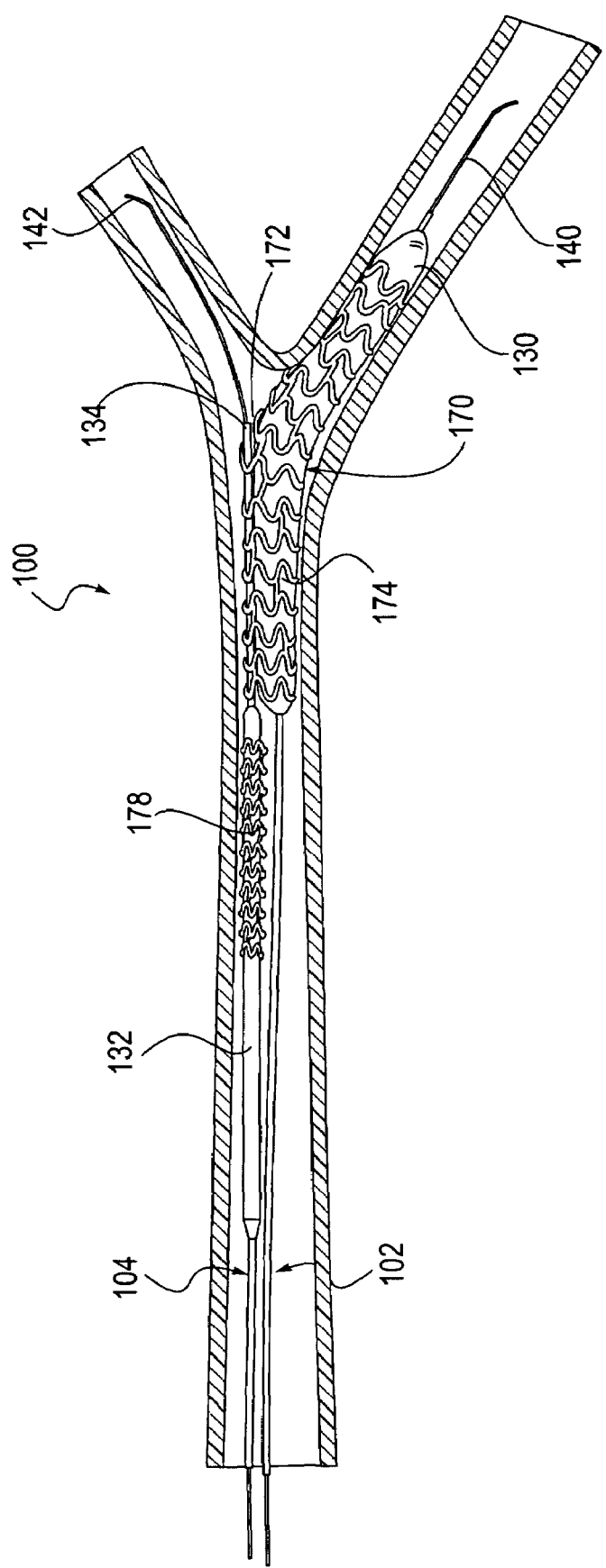
Figure 12:
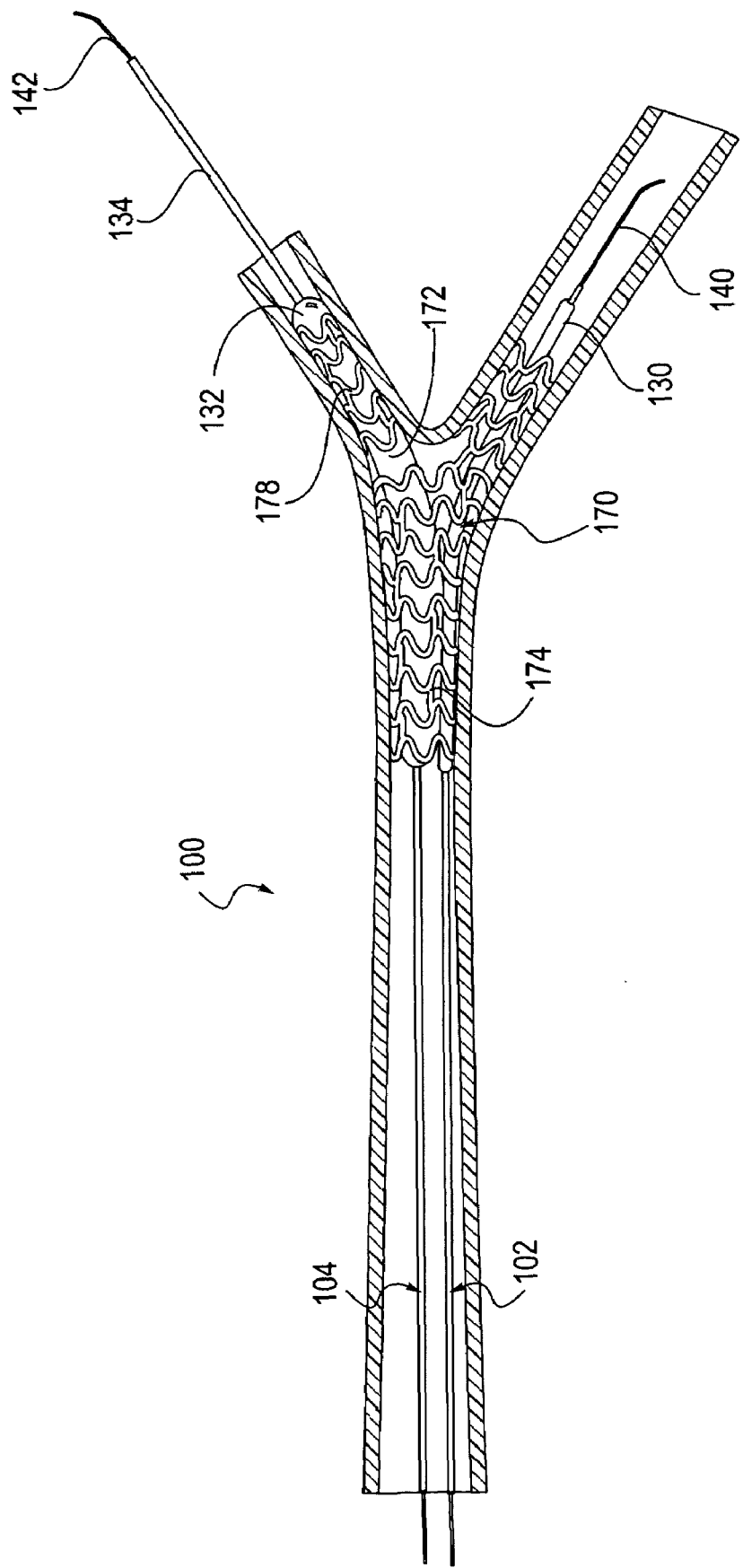
Figure 13:
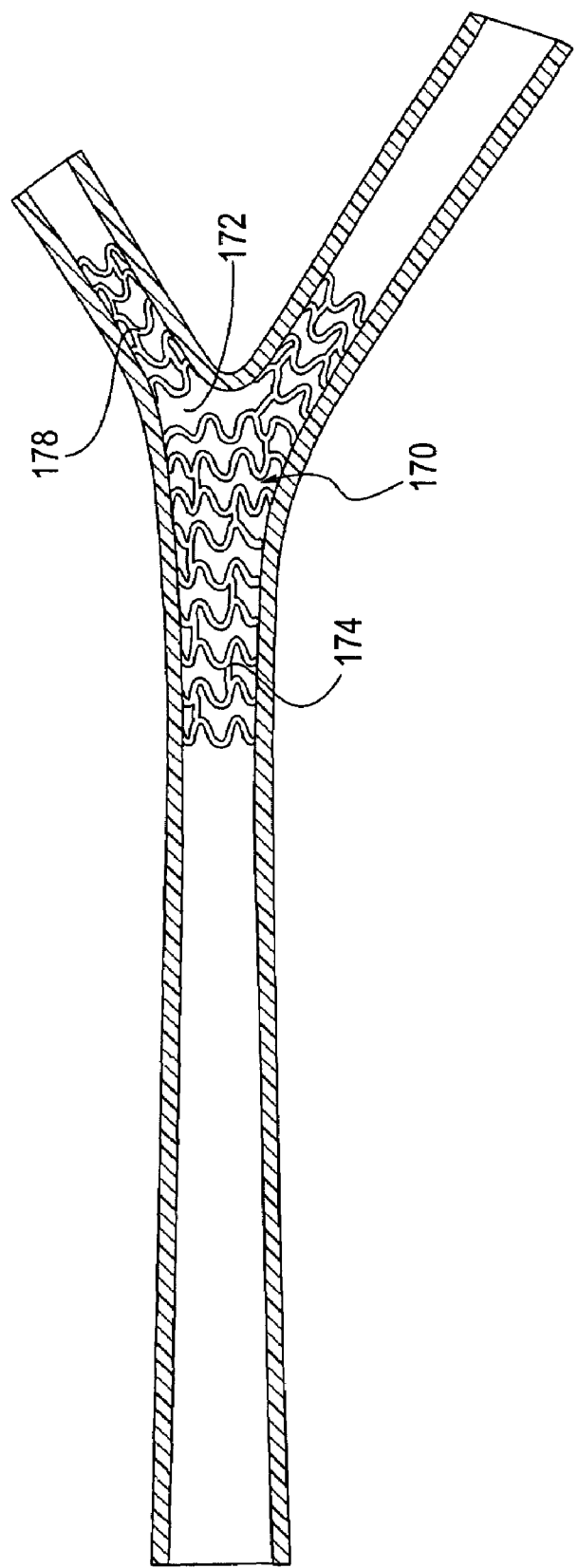

Once the main stent 170 is in the desired position, the first inflatable balloon 130 is inflated to expand the main stent 170 and to seat it securely within the vessel, as shown in FIG. 11. Then, the first inflatable balloon 130 is deflated and the linking device 160 is released so that the second balloon catheter 104 can be advanced into the second sidebranch. The second inflatable balloon 132 is inflated to expand the sidebranch stent 178 and to seat it securely within the second sidebranch vessel, while simultaneously opening the side opening 172 in the main stent 170, as shown in FIG. 12. Alternatively, if a sidebranch stent is not used or if it is to be delivered on a separate balloon catheter, the second inflatable balloon 132 is inflated to open the side opening 172 in the main stent 170 at the location of the second sidebranch vessel. Optionally, the first and second inflatable balloons 130, 132 may be inflated simultaneously using the "kissing balloons" technique.

Once the stents 170, 180 have been deployed, both balloons 130, 132 are deflated and the catheter system 100 is withdrawn from the patient. Alternatively, one or both of the balloon catheters 102, 104 can be released from the linking device 160 and used separately for dilating and/or stenting other vessels upstream or downstream of the main stent 170. Optionally, a sidebranch stent 178 may be placed in the second sidebranch vessel using a separate balloon catheter before or after deployment of the main stent 170.

Figure 14:
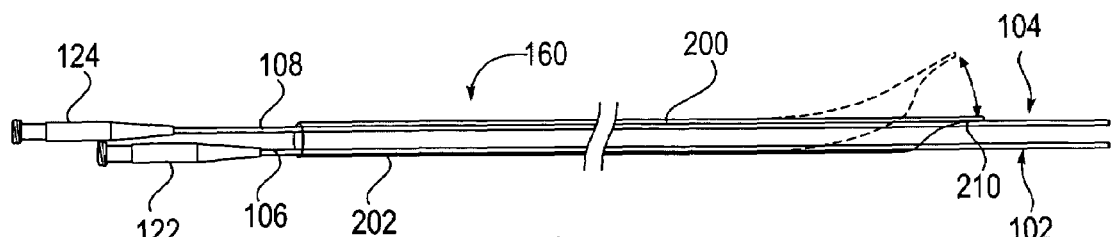
FIG. 14 shows a third embodiment of a catheter system for stenting bifurcated vessels.

FIG. 14 shows a third embodiment of a catheter system 100 for stenting bifurcated vessels utilizing a linking device 160 constructed of an elongated split-tube 200. The split-tube 200 of the linking device 160 is configured to hold the proximal sections 106, 108 of the first and second balloon catheters 102, 104 arranged in a side-by-side configuration and aligned with one another along a longitudinal axis. A longitudinal split 202 extends the length of the split-tube 200. The longitudinal split 202 allows the split-tube 200 to be placed over the proximal sections 106, 108 of the catheters 102, 104 during catheter preparation and to be removed from the catheters 102, 104 at the appropriate time during the stenting procedure. The length of the split-tube 200 can vary. Good results were obtained with a catheter system 100 having a split-tube 200 that extends along most of the proximal sections 106, 108 of the balloon catheters 102, 104 between the proximal hubs 122, 124 and the proximal guidewire ports 114, 116 of the rapid exchange catheters. Preferably, the split-tube 200 of the linking device 160 is configured with a distal pull-tab 210 or other feature to facilitate lifting the distal part of the split-tube 200 to remove the linking device 160 and release the balloon catheters 102, 104 so that they can be maneuvered separately from one another. The pull-tab 210 is preferably located on a side of the split-tube 200 opposite to the longitudinal split 202. The pull-tab 210 can be formed by skiving or cutting away part of the tube 200 as shown.

Figure 15:
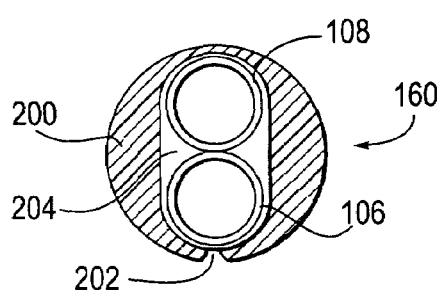
FIG. 15 shows a cross section of a split-tube linking device for the catheter system of FIG. 14.

FIG. 15 shows a cross section of one embodiment of the split-tube 200 of the linking device 160 for the catheter system 100 of FIG. 14. The split-tube 200 has an inner lumen 204 that is sized and configured to hold the proximal sections 106, 108 of the first and second balloon catheters 102, 104 together with sufficient friction that the catheter system 100 can be advanced as a unit without any relative movement of the two catheters. In one particularly preferred embodiment, the split-tube 200 is manufactured as an extruded profile with an approximately circular outer profile and an approximately oval inner lumen 204. The longitudinal split 202 connects the inner lumen 204 with the exterior of the split-tube 200 at a thin part of the wall that coincides with the major axis of the oval inner lumen 204. The longitudinal split 202 is preferably formed during the extrusion of the split-tube 200. Alternatively, the tube 200 can be extruded without the longitudinal split 202 and then slitted along the length to form the longitudinal split 202 in a secondary operation. Suitable materials for the split-tube 200 include polyamide copolymers (e.g. PEBAX 6333 or PA 8020 from ATOFINA), polypropylene, and any extrudable medical grade polymer with a suitable combination of strength, flexibility and friction characteristics.

Figure 16:
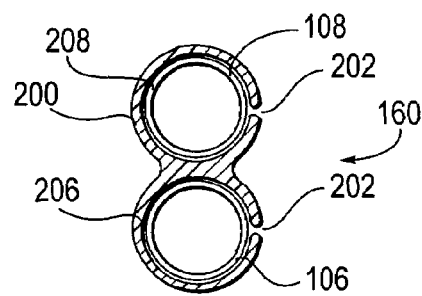
FIG. 16 shows an alternate cross section of a split-tube linking device for the catheter system of FIG. 14.

The split-tube 200 of the linking device 160 can be made with many other possible configurations, including single-lumen and multiple-lumen configurations, and may include one or more longitudinal splits 202. By way of example, FIG. 16 shows an alternate cross section of a split-tube 200 of the linking device 160 for the catheter system 100 of FIG. 14. In this embodiment, the split-tube 200 has a first inner lumen 206 that is sized and configured to hold the proximal section 106 of the first balloon catheter 102 and a second inner lumen 208 that is sized and configured to hold the proximal section 108 of the second balloon catheter 104. The inner lumens 206, 208 are sized and configured to hold the proximal sections 106, 108 of the first and second balloon catheters 102, 104 with sufficient friction that the catheter system 100 can be advanced as a unit without any relative movement of the two catheters. Two longitudinal splits 202 connect the inner lumens 206, 208 with the exterior of the split-tube 200. The two longitudinal splits 202 are preferably located on the same side of the split-tube 200 opposite to the distal pull-tab 210 to facilitate removal of the linking device 160 from both catheters 102, 104 simultaneously. The longitudinal splits 202 are preferably formed during the extrusion of the split-tube 200. Alternatively, the tube 200 can be extruded without the longitudinal splits 202 and then slitted along the length to form the longitudinal splits 202 in a secondary operation. Optionally, the linking device 160 in FIG. 15 or FIG. 16 can include additional lumens, slots or other structures to hold one or both of the guidewires 140, 142 stationary with respect to the catheter system 100.

Figure 17:
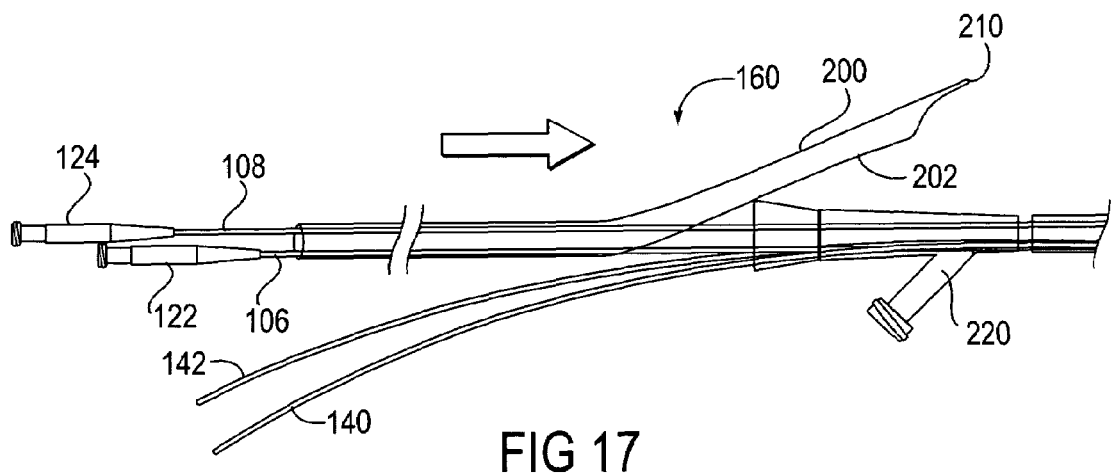
FIG. 17 shows the catheter system of FIG. 14 in use.

FIG. 17 shows the catheter system 100 of FIG. 14 in use. The linking device 160 with the split-tube 200 has the advantage that, once it is started, the split-tube 200 will demount itself as the catheter system 100 is advanced so that the physician does not need to unpeel, remove or displace a linking member that would otherwise require a "third hand". The catheter system 100 is prepared for use by aligning the first and second balloon catheters 102, 104 in the desired longitudinal alignment and then pressing the longitudinal split 202 of the split-tube 200 against the proximal sections 106, 108 of the catheters until they are enclosed within the inner lumen 204 (or lumens 206, 208) of the split-tube 200, as shown in FIG. 14. A stent or stents may then be crimped or mounted on the balloons 130, 132 in the desired configuration. This preparation may be carried out at the manufacturing facility or it may be performed at the point of use by a medical practitioner. The distal ends of the catheters 102, 104 with the stent or stents mounted thereon are inserted into the patient in the usual manner through a guiding catheter with a Y-fitting 220 or other hemostasis adapter on the proximal end of the guiding catheter. The distal pull-tab 210 is pulled toward the side to start demounting the split-tube 200 from the balloon catheters 102, 104, and then the first and second balloon catheters 102, 104 are advanced as a unit. As shown in FIG. 17, when the split-tube 200 encounters the Y-fitting 220, the split-tube 200 will peel away or demount itself from the proximal sections 106, 108 of the balloon catheters 102, 104. The stent or stents can be deployed in the vessel bifurcation using the methods described herein.

Figure 18:
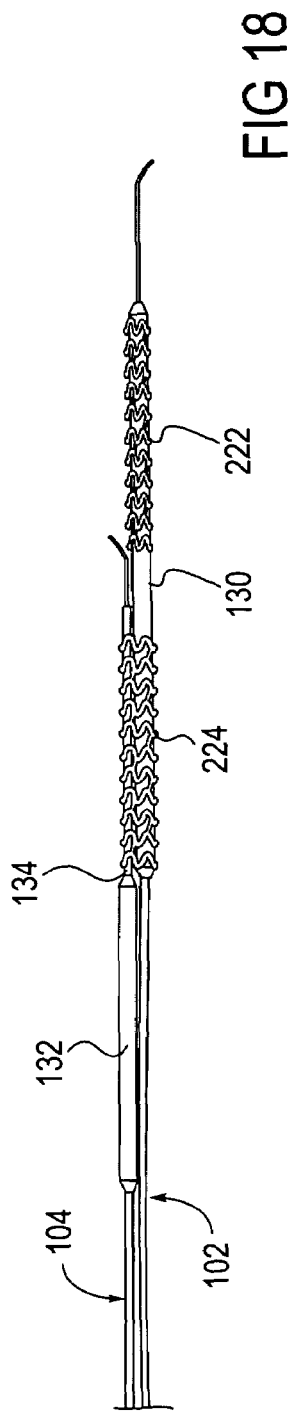
FIG. 18 shows a distal portion of a catheter system for stenting bifurcated vessels.

FIG. 18 shows a distal portion of a catheter system 100 for stenting bifurcated vessels. The catheter system 100 is similar to that shown in FIG. 5 with a first balloon catheter 102 having a first inflatable balloon 130 and a second balloon catheter 104 having a second inflatable balloon 132 and a flexible tubular extension 134 extending distally from the balloon 132. The first and second inflatable balloons 130, 132 are assembled together in a staggered or tandem initial position as shown to provide a low crossing profile. The catheter system 100 can use any of the linking devices 160 described herein to maintain the longitudinal alignment of the catheters 102, 104 during insertion. A distal stent 122 is mounted on a distal portion of the first inflatable balloon 130 and a proximal stent 124 is mounted on a proximal portion of the first inflatable balloon 130 and the flexible tubular extension 134 of the second balloon catheter 104. Preferably, only a small space is left between the distal and proximal stents 122, 124. The distal stent 122 is configured to fit the distal main branch diameter and proximal stent 124 is configured to fit the proximal main branch diameter and the bifurcation itself. Preferably, the proximal stent 124 is configured so that it can be overdilated if necessary to fit the vessel at the bifurcation. In addition, the catheter system 100 may optionally utilize a sidebranch stent 178 mounted on the second balloon 132, as illustrated in FIG. 5.

Figure 19:
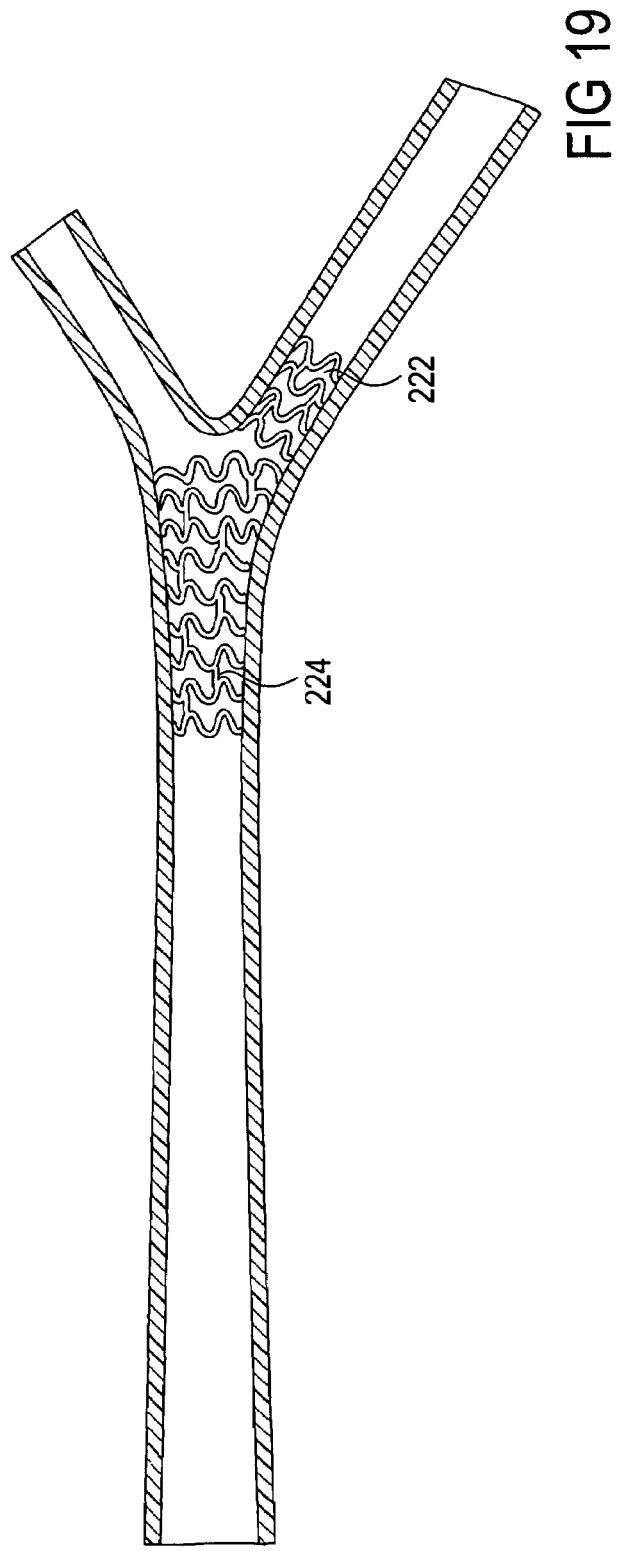
FIG. 19 shows a bifurcated vessel after stenting with the catheter system of FIG. 18.

The distal stent 122 and the proximal stent 124 are deployed using sequential and/or simultaneous inflation of the first and second inflatable balloons 130, 132 using the methods described herein. FIG. 19 shows a bifurcated vessel after stenting with the catheter system 100 of FIG. 18. Using separate distal and proximal stents 122, 124 allows the stents to be independently sized to fit the target vessel and it allows independent expansion of the two stents without any links between them that could cause distortion of one or both stents during deployment.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. Although the present invention has been primarily described in relation to angioplasty and stenting of bifurcated blood vessels, the apparatus and methods of the invention can also be used for other applications as well. For example, the catheter system can be used for stenting bifurcated lumens in other organ systems of the body. In addition, the linking devices described herein can be used in other applications where it is desired to hold two or more catheters or similar devices arranged in a side-by-side configuration and aligned with one another along a longitudinal axis. The principles of the invention can also be applied to catheters other than balloon catheters.

What is claimed is:

1. A catheter system comprising:
a first catheter having a shaft with a proximal end and a distal end;
a second catheter having a shaft with a proximal end and a distal end;
and a linking device attachable near the proximal ends of the catheters for releasably linking the first catheter and the second catheter together in a side-by-side configuration and with the first catheter and the second catheter aligned with one another along a longitudinal axis, wherein the linking device comprises an elongated split-tube releasably attaching the shaft of the first catheter and the shaft of the second catheter together.

2. The catheter system of claim 1, wherein the first catheter and the second catheter are balloon catheters.

3. The catheter system of claim 2, further comprising a stent mounted on at least one of the balloon catheters.

4. The catheter system of claim 2, wherein the first catheter and the second catheter are configured as rapid exchange balloon dilatation catheters.

5. The catheter system of claim 4, wherein a proximal section of each rapid exchange balloon dilatation catheter is constructed of hypodermic tubing joined to a flexible distal section.

6. The catheter system of claim 4, wherein at least one of the catheters comprises an elongated flexible extension tube extending distally from the dilatation balloon.

7. The catheter system of claim 5, wherein the split-tube of the linking device comprises a distal pull-tab to facilitate removal of the linking device from the shafts of the first catheter and the second catheter.

8. The catheter system of claim 7, wherein the split-tube of the linking device has a longitudinal split along one side of the split-tube and the distal pull-tab is located on a side of the split-tube opposite to the longitudinal split.

9. The catheter system of claim 7, wherein the split-tube of the linking device is configured such that separation of the split-tube from the shafts of the first catheter and the second catheter is initiated by pulling the distal pull-tab to one side, and such that the split-tube will demount itself from the shafts of the first catheter and the second catheter as the first catheter and the second catheter are advanced into a patient.

10. The catheter system of claim 5, wherein the first catheter and the second catheter are each configured with a proximal hub located at the proximal end of the shaft and a proximal guidewire port located on the shaft distal to the proximal section, and wherein the split-tube of the linking device extends along a majority of the proximal sections of the first catheter and the second catheter between the proximal hubs and the proximal guidewire ports.

11. The catheter system of claim 5, wherein the split-tube of the linking device has an inner lumen that is sized and configured to hold the proximal sections of the first catheter and the second catheter together with sufficient friction that the catheter system can be advanced as a unit without any relative longitudinal movement between the first catheter and the second catheter.

12. The catheter system of claim 11, wherein the split-tube of the linking device is made from an extruded profile with an approximately circular outer profile and an approximately oval inner lumen.

13. The catheter system of claim 12, wherein the split-tube of the linking device has a longitudinal split through a wall of the split-tube that connects the inner lumen with an exterior of the split-tube at a thin part of the wall that coincides with a major axis of the oval inner lumen.

14. The catheter system of claim 5, wherein the split-tube of the linking device has a first inner lumen that is sized and configured to hold the proximal section of the first catheter and a second inner lumen that is sized and configured to hold the proximal section of the second catheter.

15. The catheter system of claim 14, wherein the first inner lumen is sized and configured to hold the proximal section of the first catheter and the second inner lumen is sized and configured to hold the proximal section of the second catheter with sufficient friction that the catheter system can be advanced as a unit without any relative longitudinal movement between the first catheter and the second catheter.

16. The catheter system of claim 14, wherein the split-tube of the linking device has two longitudinal splits that connect the inner lumens with an exterior of the split-tube.

17. The catheter system of claim 16, wherein the split-tube of the linking device has the two longitudinal splits located along one side of the split-tube and a pull-tab is located on a side of the split-tube opposite to the longitudinal splits.

18. The catheter system of claim 14, wherein the split-tube of the linking device includes at least one additional lumen, slot or other structure to hold at least one guidewire stationary with respect to the catheter system.

19. The catheter system of claim 5, wherein the split-tube of the linking device is configured such that, after separation of the split-tube from the shafts of the first catheter and the second catheter is initiated, the split-tube will demount itself from the shafts of the first catheter and the second catheter as the first catheter and the second catheter are advanced into a patient.

20. The catheter system of claim 1, wherein the linking device is configured to hold at least one guidewire stationary with respect to the catheter system.

21. The catheter system of claim 1, wherein the first catheter and the second catheter are configured as over-the-wire catheter balloon dilatation catheters.

22. The catheter system of claim 1, wherein the split-tube is split along its entire length.

23. The catheter system of claim 1, wherein the linking device has a linked position in which the linking device links the first catheter and the second catheter and prevents longitudinal movement of the first catheter and the second catheter with respect to each other and a released position in which the first catheter and the second catheter are released to allow longitudinal movement of the first catheter and the second catheter with respect to each other.

24. A catheter system comprising:
a first rapid exchange balloon dilatation catheter having a shaft with a proximal end and a distal end, wherein a proximal section of the first rapid exchange balloon dilatation catheter is constructed of hypodermic tubing joined to a flexible distal section;
a second rapid exchange balloon dilatation catheter having a shaft with a proximal end and a distal end, wherein a proximal section of the second rapid exchange balloon dilatation catheter is constructed of hypodermic tubing joined to a flexible distal section, and an elongated flexible extension tube extending distally from the dilatation balloon;
and an elongated split-tube linking device attachable near the proximal ends of the catheters for releasably linking the first catheter and the second catheter together in a side-by-side configuration and with the first catheter and the second catheter aligned with one another along a longitudinal axis, wherein the split-tube linking device has a linked position in which the split-tube linking device links the first catheter and the second catheter and prevents longitudinal movement of the first catheter and the second catheter with respect to each other and a released position in which the first catheter and the second catheter are released to allow longitudinal movement of the first catheter and the second catheter with respect to each other, wherein the split-tube linking device has an inner lumen that is sized and configured to, when in the linked position, hold the proximal sections of the first catheter and the second catheter together with sufficient friction that the catheter system can be advanced as a unit without any relative longitudinal movement between the first catheter and the second catheter, wherein the split-tube linking device has a longitudinal split through a wall of the split-tube linking device that connects the inner lumen with an exterior of the split-tube linking device and a distal pull-tab located on a side of the split-tube linking device opposite to the longitudinal split.

25. The catheter system of claim 24, wherein the split-tube linking device is configured to be convertible from the linked position to the released position by initiating separation of the split-tube linking device from the proximal sections of the first catheter and the second catheter by pulling the distal pull-tab to the side away from the longitudinal split, and by advancing the first catheter and the second catheter into a patient, thereby causing the split-tube linking device to demount itself from the proximal sections of the first catheter and the second catheter.

26. The catheter system of claim 24, wherein the catheter system has an undeployed position in which the first rapid exchange balloon dilatation catheter and the second rapid exchange balloon dilatation catheter are initially positioned in a tandem configuration with the balloon of the first dilatation catheter positioned distal to the balloon of the second dilatation catheter, and wherein the elongated flexible extension tube of the second dilatation catheter extends alongside of the balloon of the first dilatation catheter, and wherein an expandable stent is mounted over the balloon of the first dilatation catheter and at least a portion of the elongated flexible extension tube.

27. A catheter system comprising:
a first catheter having a shaft with a proximal end and a distal end;
a second catheter having a shaft with a proximal end and a distal end;
and an elongated split-tube linking device attachable near the proximal ends of the catheters for releasably linking the first catheter and the second catheter together in a side-by-side configuration and with the first catheter and the second catheter aligned with one another along a longitudinal axis, wherein the first catheter and the second catheter are configured as rapid exchange balloon dilatation catheters.

28. The catheter system of claim 27, wherein the shaft of the first catheter and the shaft of the second catheter are each configured with a single-lumen proximal section and a two-lumen distal section and a transition between the proximal section and the distal section, an inflation lumen that extends through the single-lumen proximal section and the two-lumen distal section and is in fluid communication with an inflatable balloon mounted on the two-lumen distal section, a guidewire lumen that extends through the two-lumen distal section from a proximal guidewire port located proximal to the inflatable balloon to a distal guidewire port located distal to the inflatable balloon.

29. The catheter system of claim 28, wherein the single-lumen proximal section of each rapid exchange balloon dilatation catheter is constructed of hypodermic tubing joined to a flexible distal section.

30. The catheter system of claim 27, wherein the linking device has a linked position in which the linking device links the first catheter and the second catheter and prevents longitudinal movement of the first catheter and the second catheter with respect to each other such that the catheter system can be advanced as a unit without any relative longitudinal movement between the first catheter and the second catheter and a released position in which the first catheter and the second catheter are released to allow longitudinal movement of the first catheter and the second catheter with respect to each other.

31. The catheter system of claim 27, further comprising a stent mounted on at least one of the balloon catheters.

32. The catheter system of claim 27, wherein the linking device comprises a split-tube releasably attaching the shaft of the first catheter and the shaft of the second catheter together.

33. The catheter system of claim 27, wherein at least one of the catheters comprises an elongated flexible extension tube extending distally from the dilatation balloon.

34. The catheter system of claim 27, wherein the linking device is configured to hold at least one guidewire stationary with respect to the catheter system.

35. The catheter system of claim 27, wherein the linking device comprises a body with a first channel and a second channel arranged in a side-by-side configuration, the first channel being configured to releasably hold the shaft of the first catheter and the second channel being configured to releasably hold the shaft of the second catheter.

36. The catheter system of claim 27, wherein the linking device comprises a body with a first channel and a second channel arranged in a side-by-side configuration, a first locking device associated with the first channel configured to releasably hold the shaft of the first catheter, and a second locking device associated with the second channel configured to releasably hold the shaft of the second catheter.

37. The catheter system of claim 27, wherein the linking device comprises a first linking member attached to the shaft of the first catheter and a second linking member attached to the shaft of the second catheter, the first linking member and the second linking member have interlocking features so that the first linking member and the second linking member can be releasably attached to one another.

38. The catheter system of claim 27, wherein the linking device comprises a peel-away sheath releasably attaching the shaft of the first catheter and the shaft of the second catheter together.

39. The catheter system of claim 27, wherein the linking device comprises a split-tube releasably attaching the shaft of the first catheter and the shaft of the second catheter together.

40. The catheter system of claim 39, wherein the split-tube is split along its entire length.

41. The catheter system of claim 39, wherein the split-tube of the linking device comprises a distal pull-tab to facilitate removal of the linking device from the shafts of the first catheter and the second catheter.

42. The catheter system of claim 41, wherein the split-tube of the linking device has a longitudinal split along one side of the split-tube and the distal pull-tab is located on a side of the split-tube opposite to the longitudinal split.

43. The catheter system of claim 41, wherein the split-tube of the linking device is configured such that separation of the split-tube from the shafts of the first catheter and the second catheter is initiated by pulling the distal pull-tab to one side, and such that the split-tube will demount itself from the shafts of the first catheter and the second catheter as the first catheter and the second catheter are advanced into a patient.

44. The catheter system of claim 39, wherein the first catheter and the second catheter are each configured with a proximal hub located at the proximal end of the shaft and a proximal guidewire port located on the shaft distal to the proximal section, and wherein the split-tube of the linking device extends along a majority of the proximal sections of the first catheter and the second catheter between the proximal hubs and the proximal guidewire ports.

45. The catheter system of claim 44, wherein the split-tube of the linking device has an inner lumen that is sized and configured to hold the proximal sections of the first catheter and the second catheter together with sufficient friction that the catheter system can be advanced as a unit without any relative longitudinal movement between the first catheter and the second catheter.

46. The catheter system of claim 45, wherein the split-tube of the linking device is made from an extruded profile with an approximately circular outer profile and an approximately oval inner lumen.

47. The catheter system of claim 46, wherein the split-tube of the linking device has a longitudinal split through a wall of the split-tube that connects the inner lumen with an exterior of the split-tube at a thin part of the wall that coincides with a major axis of the oval inner lumen.

48. The catheter system of claim 44, wherein the split-tube of the linking device has a first inner lumen that is sized and configured to hold the proximal section of the first catheter and a second inner lumen that is sized and configured to hold the proximal section of the second catheter.

49. The catheter system of claim 48, wherein the first inner lumen is sized and configured to hold the proximal section of the first catheter and the second inner lumen is sized and configured to hold the proximal section of the second catheter with sufficient friction that the catheter system can be advanced as a unit without any relative longitudinal movement between the first catheter and the second catheter.

50. The catheter system of claim 48, wherein the split-tube of the linking device has two longitudinal splits that connect the inner lumens with an exterior of the split-tube.

51. The catheter system of claim 50, wherein the split-tube of the linking device has the two longitudinal splits located along one side of the split-tube and a pull-tab is located on a side of the split-tube opposite to the longitudinal splits.

52. The catheter system of claim 48, wherein the split-tube of the linking device includes at least one additional lumen, slot or other structure to hold at least one guidewire stationary with respect to the catheter system.

53. The catheter system of claim 39, wherein the split-tube of the linking device is configured such that, after separation of the split-tube from the shafts of the first catheter and the second catheter is initiated, the split-tube will demount itself from the shafts of the first catheter and the second catheter as the first catheter and the second catheter are advanced into a patient.

* * * * *